United States Patent
Slattery et al.

(10) Patent No.: US 10,835,721 B2
(45) Date of Patent: Nov. 17, 2020

(54) DELIVERY SYSTEM FOR A DRUG COATED ANGIOPLASTY BALLOON

(71) Applicant: Merit Medical Ireland Limited, Dublin (IE)

(72) Inventors: David Slattery, Kinvara (IE); Jonathan Akehurst, Armagh (GB); David Kelly, Ardrahan (IE); John Joseph Kelly, Naas (IE)

(73) Assignee: Merit Medical Ireland Limited, South Jordan, UT (US)

( * ) Notice: Subject to any disclaimer, the term of this patent is extended or adjusted under 35 U.S.C. 154(b) by 458 days.

(21) Appl. No.: 15/735,556

(22) PCT Filed: Jun. 10, 2016

(86) PCT No.: PCT/EP2016/063398
§ 371 (c)(1),
(2) Date: Dec. 11, 2017

(87) PCT Pub. No.: WO2016/198670
PCT Pub. Date: Dec. 15, 2016

(65) Prior Publication Data
US 2018/0353733 A1 Dec. 13, 2018

(30) Foreign Application Priority Data

Jun. 12, 2015 (EP) .................................... 15171959
Sep. 15, 2015 (EP) .................................... 15185285
Apr. 8, 2016 (EP) .................................... 16164520

(51) Int. Cl.
*A61M 25/10* (2013.01)

(52) U.S. Cl.
CPC ..... *A61M 25/104* (2013.01); *A61M 2025/105* (2013.01); *A61M 2025/1081* (2013.01)

(58) Field of Classification Search
CPC .......... A61M 25/10; A61M 2025/1043; A61M 2025/1084; A61M 2025/1088;
(Continued)

(56) References Cited

U.S. PATENT DOCUMENTS

| 6,884,257 B1 | 4/2005 | Cox |
| 2003/0144683 A1 | 7/2003 | Sirhan et al. |

(Continued)

FOREIGN PATENT DOCUMENTS

| EP | 0 442 657 A2 | 8/1991 |
| EP | 0 442 657 A3 | 8/1991 |
| WO | 2015077545 | 5/2015 |

OTHER PUBLICATIONS

International Search Report issued in PCT/EP2016/063398; dated Sep. 12, 2016.
(Continued)

*Primary Examiner* — Jason E Flick
(74) *Attorney, Agent, or Firm* — Stoel Rives LLP (57) ABSTRACT

A delivery system includes a catheter, and a drug coated angioplasty balloon mounted on the catheter. The balloon has a wrapped or folded delivery configuration and an expanded deployed configuration. A protective sleeve surrounds the drug coated balloon in the delivery configuration to minimise wash-off of drug from the balloon during delivery. The protective sleeve is retractable, so that once the drug coated balloon is at or near the treatment site, the sleeve can be retracted to allow the drug coated balloon to operate effectively. The protective sleeve can have a spacer mounted to or integral with the protective sleeve. The spacer in one case can comprise of interior ribs or ridges on the sleeve which minimise the surface area of the sleeve in direct contact with the drug coating on the balloon.

18 Claims, 7 Drawing Sheets

(58) Field of Classification Search
CPC .... A61M 2025/105; A61M 2025/1081; A61M 25/104
See application file for complete search history.

(56) References Cited

U.S. PATENT DOCUMENTS

| | | |
|---|---|---|
| 2004/0215223 A1 | 10/2004 | Shaw et al. |
| 2005/0038383 A1 | 2/2005 | Kelley et al. |
| 2009/0105686 A1* | 4/2009 | Snow .................. A61M 25/10 604/509 |
| 2010/0228333 A1 | 9/2010 | Drasler |
| 2011/0270226 A1* | 11/2011 | Kocur ............... A61M 25/1029 604/509 |
| 2012/0277843 A1 | 11/2012 | Weber |
| 2012/0296313 A1* | 11/2012 | Andreacchi ....... A61M 25/0668 604/509 |
| 2012/0324696 A1 | 12/2012 | Liu |
| 2019/0344054 A1 | 11/2019 | Slattery et al. |

OTHER PUBLICATIONS

Written Opinion issued in PCT/EP2016/063398; dated Sep. 12, 2016.
The extended European search report issued by the European Patent Office dated Oct. 19, 2016, which corresponds to European Patent Application No. 16164520.5-1501.
International Search Report and Written Opinion dated Dec. 13, 2017 for PCT/EP2017/074852.

* cited by examiner

DELIVERY SYSTEM FOR A DRUG COATED ANGIOPLASTY BALLOON

INTRODUCTION

The present invention relates to a protective sleeve for a drug coated angioplasty balloon, which is designed to protect and preserve a drug coating during insertion into the body and delivery to a treatment site in the coronary or peripheral vasculature.

BACKGROUND

Coronary artery disease and peripheral artery disease are both major and growing health problems throughout the world, associated with aging populations and lifestyle changes. Both diseases are characterised by atherosclerosis, which is the build-up of plaque or fatty deposits on the inside of the arteries, resulting in the arteries becoming blocked or narrowed. In the coronary arteries, this can result in reduced blood flow to and oxygenation of the heart, leading to angina and heart attack. In the peripheral arteries, this can result in reduced blood flow to the affected organs/limbs, which can have many severe consequences such as chronic limb ischemia and diabetic foot, potentially requiring amputation.

Occluded, stenotic, or narrowed blood vessels may be treated with a number of relatively non-invasive medical procedures including percutaneous transluminal angioplasty, stenting and atherectomy. Angioplasty techniques typically involve the use of a balloon dilatation catheter. The balloon dilatation catheter is advanced over a guidewire so that the balloon is positioned adjacent a stenotic lesion. The balloon is then inflated, compressing the plaque against the vessel wall and the restriction of the vessel is opened.

One of the major limitations of traditional balloon angioplasty in treating coronary artery disease and peripheral artery disease is re-stenosis, which is the re-narrowing of the artery post procedure. Drug coated angioplasty balloons ("DCB"s) have been developed, comprising polymer balloons coated with a solution comprising a mix of an antiproliferate drug such as Paclitaxel and an excipient/carrier, which is absorbed quickly into the vessel wall when the balloon is inflated. Treatment using DCBs has been demonstrated to reduce the level of re-stenosis and maintain the patency of treated arteries post procedure.

However, one of the known limitations of DCB's currently available for use is the substantial loss of drug coating, or "wash-off", en-route to the site of the stenosis in the vasculature. It is known that a significant portion of drug coating is lost or 'washed off' from the moment when the drug coated balloon catheter first enters the body (usually in the femoral artery in the groin) and begins being advanced through the vasculature, until it reaches intended treatment site, i.e. the location of the stenosis. Developers of DCB's have attempted to address this problem by developing more durable coatings using different excipients/carriers; however with limited success, as there is a natural trade-off between minimising "wash off" of drug en-route and ensuring optimum drug absorption at the treatment site.

US20120277843A describes a medical balloon with folds on which lines are disposed and a therapeutic agent is located between the lines.

There is an ongoing need for a solution to the problem of drug loss during insertion and delivery of a drug coated balloon.

STATEMENTS OF INVENTION

According to the invention there is provided a delivery system comprising:

a catheter;

a drug coated angioplasty balloon mounted on the catheter, the balloon having a wrapped or folded delivery configuration and an expanded deployed configuration; and a protective sleeve surrounding the drug coated balloon in the delivery configuration to minimise wash-off of drug from the balloon during delivery.

The system may comprise a spacer to at least partially space-apart the protective sleeve from the drug coating on the balloon when the balloon is in the wrapped or folded delivery configuration. The spacer is mounted to or integral with the protective sleeve.

In one embodiment the sleeve is movable to facilitate movement of the balloon to the deployed configuration.

The sleeve may be configured to split or rupture on expansion of the balloon. In one case a distal end of the sleeve extends to a distal end of the balloon and the sleeve has a slit or a region of weakness which splits or ruptures on inflation of the balloon.

The sleeve may alternatively or additionally be configured to split or rupture by pulling the proximal end of the sleeve away from the distal end of the balloon. In this case a distal end of the sleeve extends to a distal end of the balloon and the sleeve has a slit or a region of weakness which splits of ruptures through the pulling action on the sleeve.

The spacer may comprise at least one ridge or rib extending along the interior surface of the protective sleeve.

In some embodiments the sleeve is retractable prior to, during, or after expansion of the balloon. In one case the sleeve has an extension to the proximal end of the catheter.

In one embodiment the system comprises a coupling between the protective sleeve and the catheter. In one case the protective sleeve and the catheter are coupled for delivery and de-coupled for deployment of the balloon.

In some embodiments the coupling comprises coupling elements on the protective sleeve and the catheter. The coupling elements may be interengagable elements, for example, threads. The coupling may in some cases be quick release; luer tapers; Tuohy Borst or the like.

According to one aspect of the invention, there is provided a protective sleeve for a drug coated angioplasty balloon, comprising an elongate polymer tube membrane, which surrounds and fully encases the drug coated balloon in its original folded/wrapped configuration.

The protective sleeve has a tapered distal end section which runs tightly to the distal tip of the balloon and which is designed to split or rupture once the balloon is inflated, or the sleeve is pulled back by the operator, thereby allowing the protective sleeve to be withdrawn and the drug coated balloon to be exposed to the vessel wall.

The protective sleeve can have multiple linear ridges or ribs extending longitudinally along the interior surface of the polymer tube and spaced equidistantly from one another, which are designed to minimise the surface area of the sleeve coming in direct contact with the drug coating of the balloon. The ridges or ribs also provide added column strength for advancing through a lesion.

The protective sleeve material comprises a polymeric material, preferably Polytetrafluoroethylene (PTFE), Polyethylene terephthalate (PET), Nylon, or PolyEtherEtherKetone (PEEK). The material must be sufficiently strong and durable to prevent damage to, or perforation of the protective sleeve during insertion and delivery. The inner surface of the protective sleeve can have a sufficiently lubricious coating to minimise friction with the drug coated abluminal surface of the balloon and ensure ease of withdrawal of the protective sleeve.

The drug coated balloon catheter equipped with the protective sleeve is inserted and advanced to the intended treatment site in the coronary or peripheral vasculature in the normal manner.

In the invention, a sleeve for a drug coated balloon is provided which provides protection for the drug coating to inhibit wash-off without any modification to the balloon. Thus, the balloon may be used for the intended treatment, independent of the sleeve.

In one embodiment, the protective sleeve is attached to the catheter outer shaft at the proximal end of the balloon. In this embodiment, once the balloon is inflated, the protective sleeve splits from the distal end along the entire length of the balloon and peels away from the balloon, thereby exposing the full length of the balloon's coated abluminal surface to the vessel wall. In this embodiment, the protective sleeve remains attached to the catheter outer shaft at the proximal end of the balloon during the angioplasty treatment and is removed along with the catheter, once the balloon is subsequently deflated.

According to the invention there is provided a delivery system, comprising of a catheter and a protective sleeve positioned over the balloon. On the distal portion of the catheter, the protective sleeve has a tapered distal end section which runs tightly to the distal tip of the balloon and which is designed to split or rupture once the balloon is inflated.

On the proximal portion of the protective sleeve, a female threaded ring is coupled to the protective sleeve. This allows the protective sleeve to become stationary relative to the catheter.

On the catheter proximal to the balloon a male threaded ring is coupled to the outer. After the tapered distal section is ruptured, the catheter is torqued to unscrew the thread. This then allows the protective sleeve to become free, and the sleeve is allowed to move proximally thereby exposing the full length of the balloon's coated abluminal surface to the vessel wall.

After the angioplasty treatment the catheter is withdrawn back into the protective sleeve and screwed back into its thread and removed along with the catheter from the body.

In a second embodiment, the protective sleeve is not attached to the catheter outer shaft, but instead extends outside the catheter shaft along almost the entire length of the catheter shaft. This length is determined by the length of the balloon that will be used and terminates in a manifold near the proximal end of the catheter shaft. The manifold has a port and a locking mechanism that allows the protective sleeve to lock onto the catheter outer shaft. Such a mechanism could include a Tuohy Borst type seal. In this embodiment, the port may be used to remove air from the space between catheter and sleeve, either by pulling a vacuum or introducing a liquid to displace the air. The protective sleeve is retracted from the balloon by unlocking the mechanism and pulling back on the manifold thereby exposing the full length of the balloon's coated abluminal surface to the vessel wall. The protective sheath is removed along with the catheter, once the balloon is subsequently deflated.

In a third embodiment, the protective sleeve is not attached to the catheter outer shaft, but instead extends outside the catheter shaft along almost the entire length of the catheter shaft. This length is determined by the length of the balloon that will be used and terminates in a manifold near the proximal end of the catheter shaft. In this embodiment, the protective sleeve is retracted from the balloon by pulling back on the manifold thereby exposing the full length of the balloon's coated abluminal surface to the vessel wall. The protective sheath is removed along with the catheter, once the balloon is subsequently deflated.

The invention also provides a method of performing a balloon dilation procedure within a patients vascular system comprising:
  providing a drug coated balloon mounted on a catheter with a protective sleeve surrounding the drug coating on the balloon, the balloon having a wrapped or folded delivery configuration and an expanded deployed configuration;
  advancing the catheter to a treatment location with the balloon in the delivery configuration;
  removing the sleeve from the balloon to expose the drug coated surface of the balloon;
  carrying out a treatment using the drug coated balloon; and removing the catheter.

In one embodiment the method comprises:
  providing a delivery system of the invention;
  advancing the catheter to a treatment location with the balloon in the delivery configuration;
  removing the sleeve from the balloon to expose the drug coated surface of the balloon; and
  carrying out a treatment using the drug coated balloon.

The method may comprise the step of applying a force to the sleeve to remove the sleeve from the balloon.

In one case the method comprises at least partially inflating the balloon to remove the sleeve from the balloon.

Alternatively or additionally the method comprises pulling the sleeve proximally to remove the sleeve from the balloon.

In one embodiment the sleeve is removed prior to inflation of the balloon.

BRIEF DESCRIPTION OF THE DRAWINGS

The invention will now be described with reference to the accompanying drawings which show embodiments of the protective sleeve for a drug coated angioplasty balloon according to the invention in which.

DETAILED DESCRIPTION

Referring to the drawings and initially to FIGS. 1 to 6 thereof there is illustrated a delivery system 1 for a drug coated angioplasty balloon. The delivery system comprises a balloon catheter 2 which has a distal tip 3 and a proximal manifold 4 having an inflation port 6 through which air or liquid is delivered to inflate a drug coated balloon 5 mounted at the distal end of the catheter 2. The balloon 5 has a wrapped or folded delivery configuration and an expanded/inflated deployed configuration. In the invention a protective sleeve 10 surrounds the drug coated balloon 5 in the delivery configuration to minimise wash-off of drug from the balloon during delivery.

Figure 4:
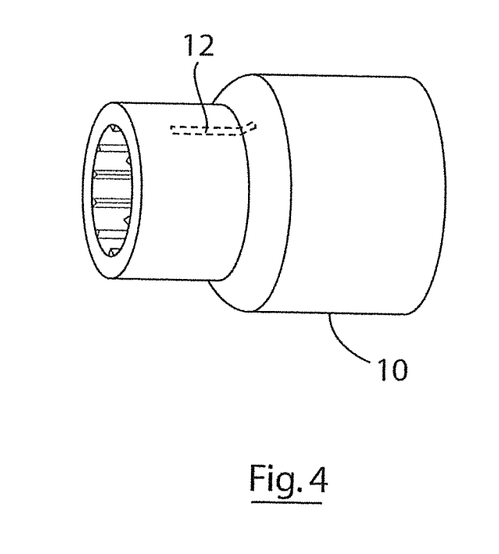
FIG. 4 is an enlarged view of a distal end of the protective sleeve.
Figure 5:
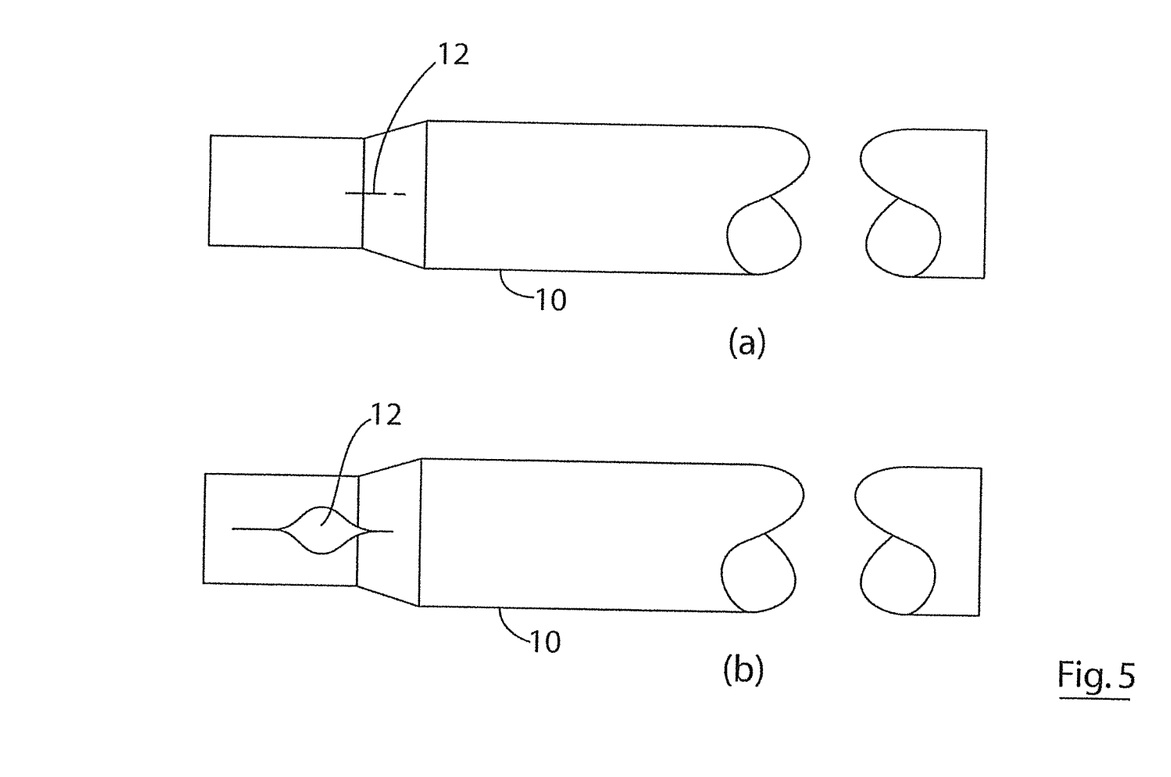
FIGS. 5(a) to 5(b) are a series of images illustrating the propagation of the slit at the distal end of the sleeve.
Figure 6:
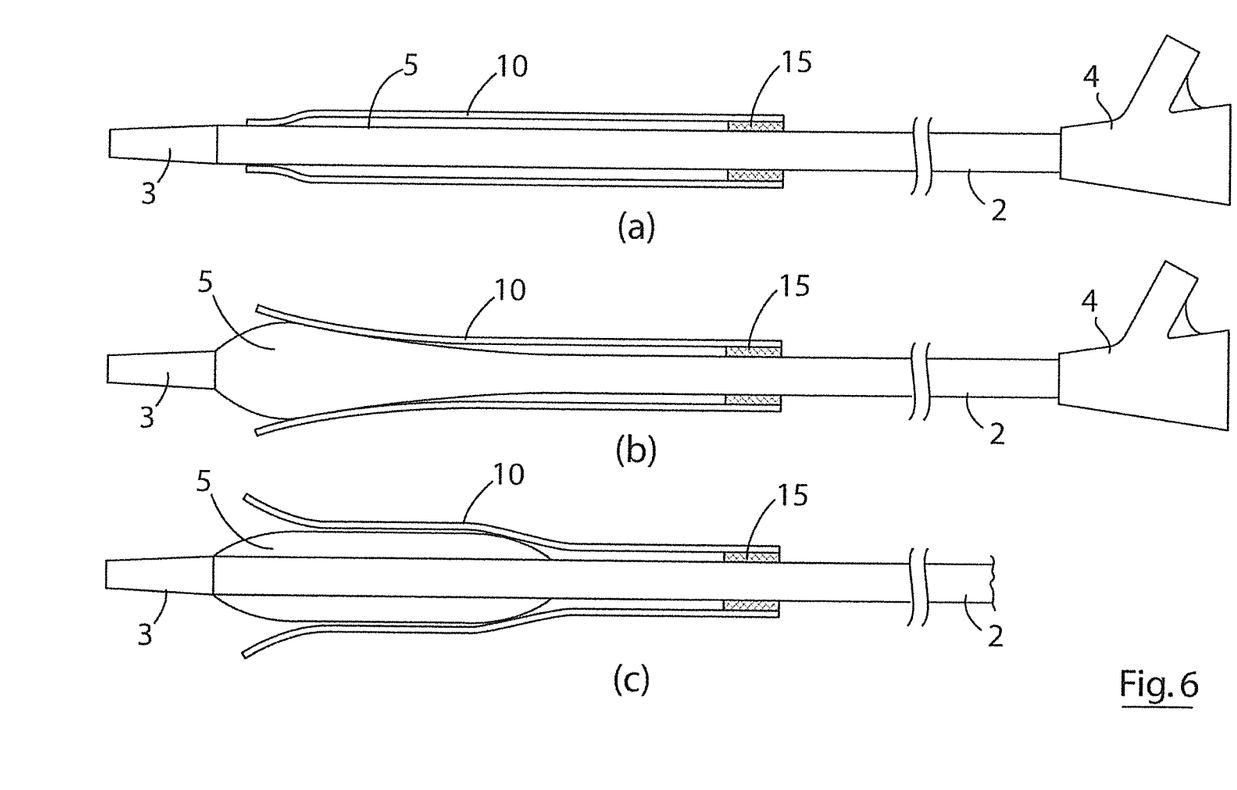
FIGS. 6(a) to 6(c) are a series of images illustrating the progressive release of the protective sleeve from the balloon.

Referring especially to FIG. 4 it will be noted that the sleeve 10 has a region of weakness such as a slit 12 or the like near the distal end of the sleeve 10. The tapered distal end section of the sleeve 10 advantageously runs tightly to the distal tip of the balloon 5 and is designed to split or rupture as the balloon is inflated. Following initial inflation of the balloon to a low pressure to split the sleeve, the balloon is deflated, and the sleeve is then pulled away from the distal end of the catheter. Alternatively, spitting of the sleeve can be achieved by pulling the sleeve away from distal end of the catheter prior to inflation of the balloon. Another alternative is to combine pulling of the sleeve with inflation of the balloon to a low pressure. In all these cases, the removal of the sleeve allows the drug coated balloon to be exposed to the vessel wall.

The protective sleeve material comprises a polymeric material, preferably Polytetrafluoroethylene (PTFE), Polyethylene terephthalate (PET), Nylon or PolyEtherEtherKetone (PEEK). The material is sufficiently strong and durable to prevent damage to, or perforation of the protective sleeve during insertion and delivery. The inner surface of the protective sleeve can have a sufficiently lubricious coating to minimise friction with the drug coated abluminal surface of the balloon and ensure ease of withdrawal of the protective sleeve 10.

Figure 1:
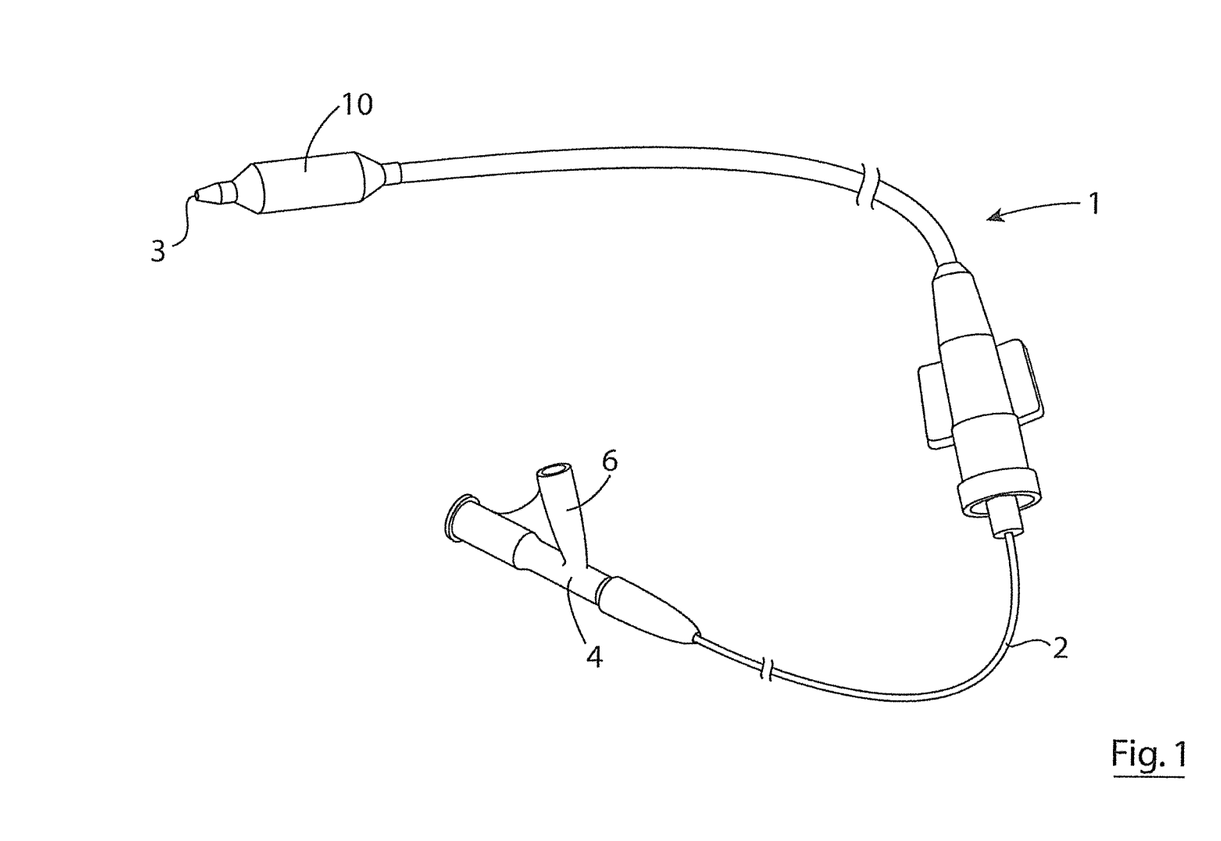
FIG. 1 is a perspective view of a delivery system for a drug coated angioplasty balloon according to the invention.
Figure 2:
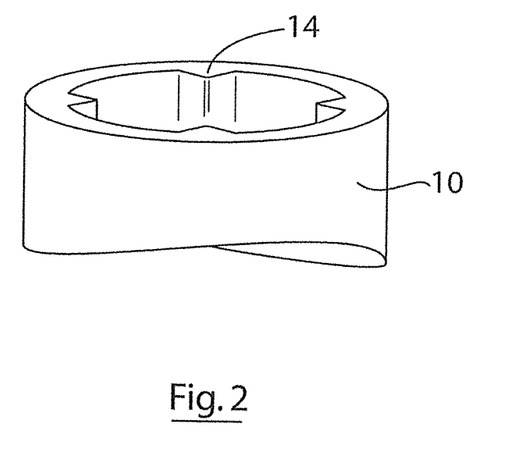
FIG. 2 is a cut-away view of a protective sleeve.
Figure 3:
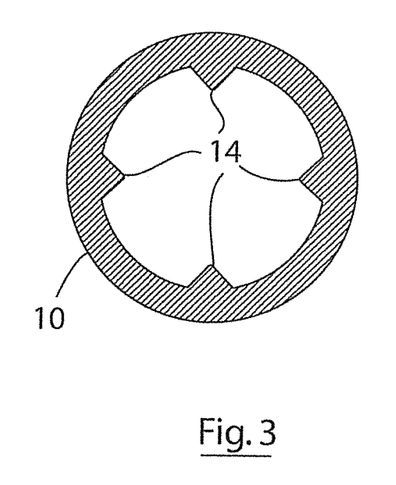
FIG. 3 is a cross sectional view of the sleeve.

Referring especially to FIGS. 2 and 3 the protective sleeve can have multiple linear ridges or ribs 14 extending longitudinally along the interior surface of the polymer tube and spaced equidistantly from one another, which are designed to minimise the surface area of the sleeve 10 coming in direct contact with the drug coating of the balloon 5. The ridges or ribs 14 also provide added column strength for advancing through a lesion.

The drug coated balloon catheter equipped with the protective sleeve 10 is inserted and advanced to the intended treatment site in the coronary or peripheral vasculature in the normal manner.

In one embodiment, a proximal end 15 of the protective sleeve 10 is attached to the catheter outer shaft at the proximal end of the balloon 5. In this embodiment, once the balloon 5 is inflated, the protective sleeve 10 splits from the distal end along the entire length of the balloon and peels away from the balloon, thereby exposing the full length of the balloon's coated abluminal surface to the vessel wall. In this case, the protective sleeve 10 can remain attached to the catheter outer shaft at the proximal end of the balloon during the angioplasty treatment and is removed along with the catheter, once the balloon 5 is subsequently deflated. Such an arrangement is suitable for a rapid exchange type delivery system.

Figure 7:
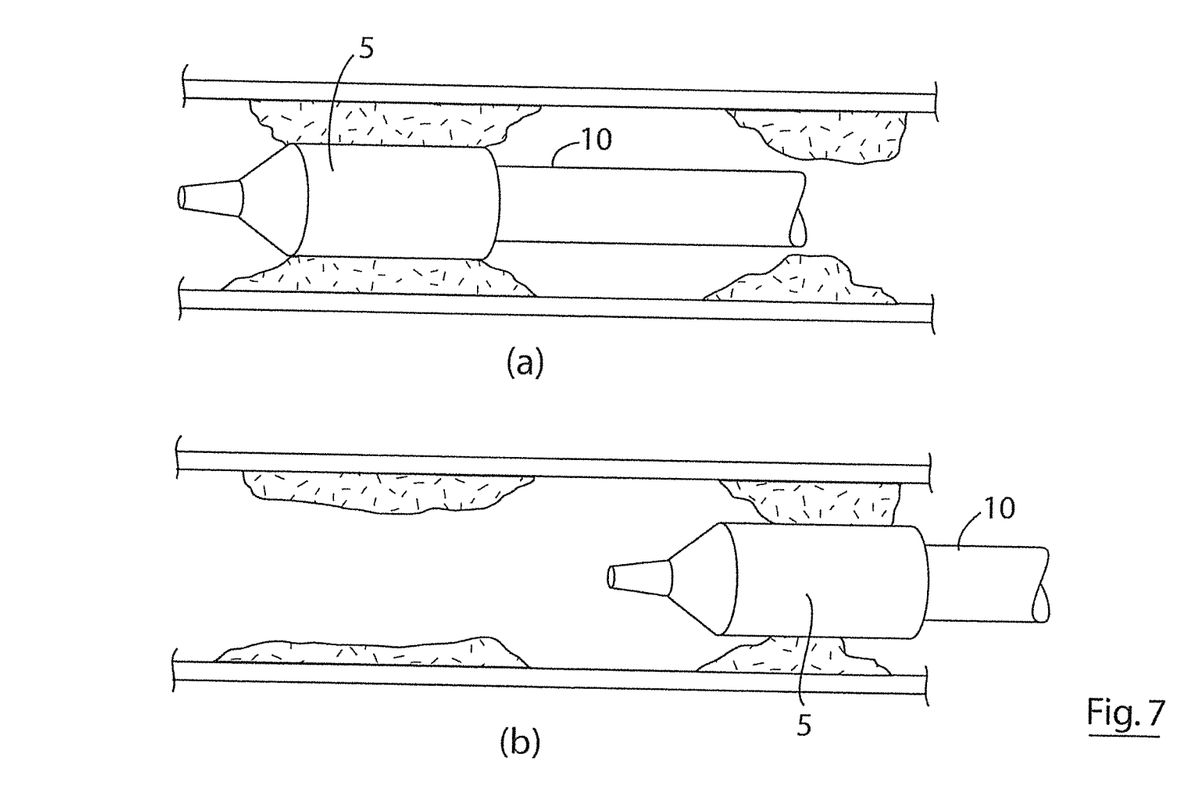
FIGS. 7(a) to 7(b) illustrate retraction of the protective sleeve for different lengths to treat a number of lesions.

In another case the sleeve 10 has an extension to a proximal end of the catheter which allows a clinician to retract the sleeve to any desired location. This retraction can be aided by visualisation, for example by providing one or more markers on the sleeve and/or catheter. FIGS. 7(a) to 7(b) illustrate an example of such a system, in use in treating multiple lesions. FIG. 7(a) shows the sleeve 10 being retracted sufficiently to allow a section of the balloon 5 to treat a distal lesion. FIG. 7(b) shows the sleeve 10 retracted further for treatment of another lesion. Many variations are possible to facilitate treatment of multiple and/or complex lesions.

In some cases the protective sleeve 10 and the catheter are coupled for delivery and de-coupled for deployment of the balloon 5. The coupling may comprise interengagable elements on the protective sleeve 10 and the catheter. One example involves the use of a threaded coupling.

Figure 8:
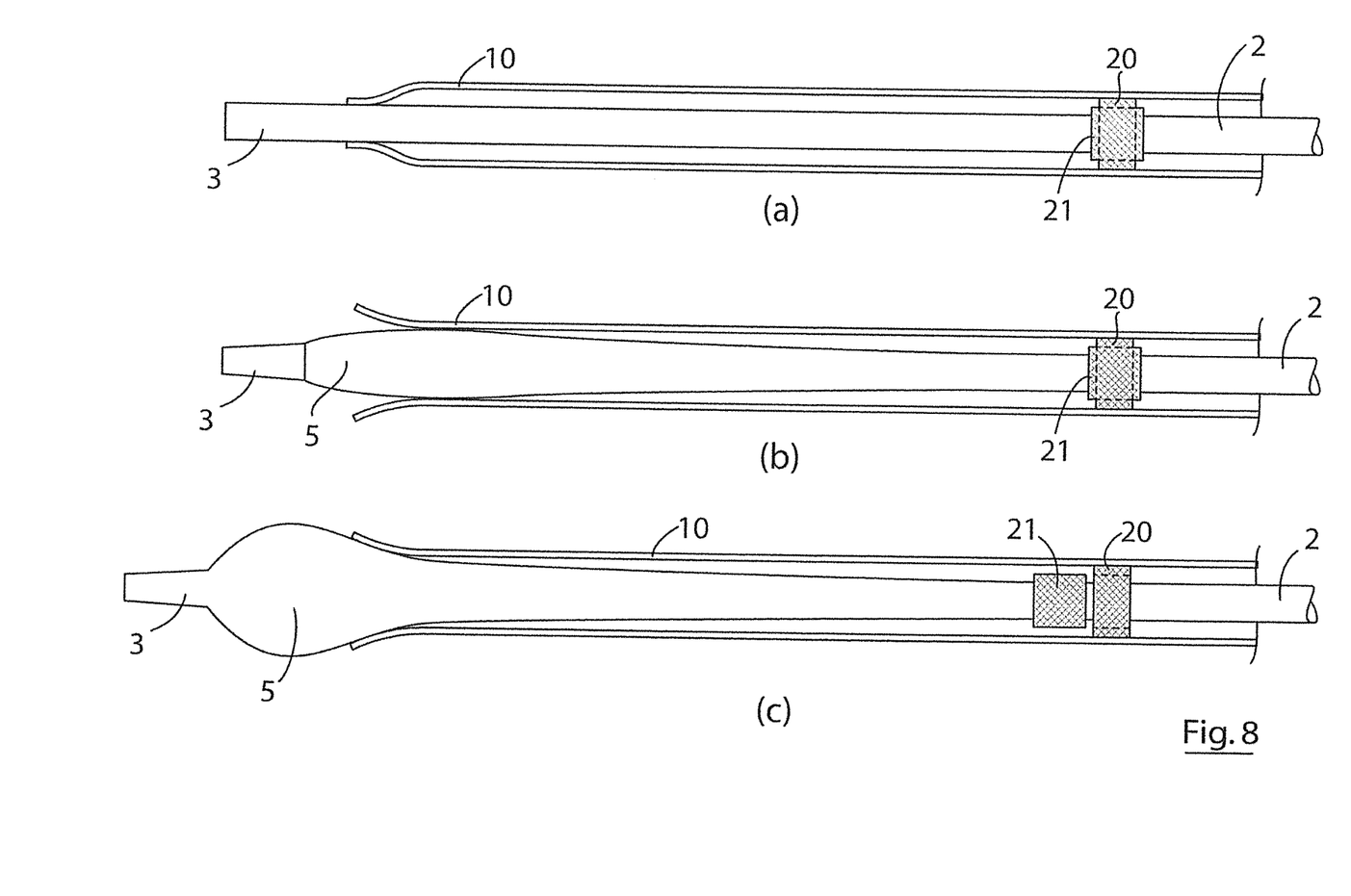
FIGS. 8(a) to 8(c) are a series of images illustrating the operation of a coupling between a protective sleeve and a catheter.

FIGS. 8(a) to 8(c) in this case the coupling comprises a first coupling part 20 on the inside of the protective sleeve 10 and a second coupling part 21 on the outside of the catheter.

On the proximal portion of the protective sleeve 10, a female threaded ring 20 is coupled to the protective sleeve 10. This allows the protective sleeve 10 to become stationary relative to the balloon.

On the catheter proximal to the balloon a male threaded ring 21 is coupled to the outer. After the tapered distal section of the sleeve 10 is ruptured, the catheter is torqued to unscrew the thread. This then allows the protective sleeve to become free and be withdrawn.

The catheter is then allowed to move distally out of the protective sleeve 10, thereby exposing the full length of the balloon's coated abluminal surface to the vessel wall.

After the angioplasty treatment the catheter is withdrawn back into the protective sleeve and screwed back into its thread and removed along with the catheter from the body. Such an arrangement is suitable for a rapid exchange delivery system.

It will of course be understood that the invention is not limited to the specific details as herein described, which are given by way of example only, and that various alterations and modifications are possible without departing from the scope of the invention.

The invention claimed is:

1. A drug coated angioplasty balloon delivery system comprising:
 a catheter;
 a drug coated angioplasty balloon mounted on the catheter, the balloon having a wrapped or folded delivery configuration and an expanded deployed configuration;
 a protective sleeve surrounding the drug coated balloon in the delivery configuration to minimize wash-off of drug from the balloon during delivery; and
 a spacer to least partially space-apart the protective sleeve from the drug coating on the balloon when the balloon is in the wrapped or folded configuration,
 wherein the spacer extends longitudinally along an interior surface of the protective sleeve.

2. The delivery system as claimed in claim 1 wherein the spacer is mounted to or integral with the protective sleeve.

3. The delivery system as claimed in claim 1 wherein the sleeve is movable or removable to facilitate movement of the balloon to the deployed configuration.

4. The delivery system as claimed in claim 3 wherein the sleeve is configured to split or rupture on expansion of the balloon.

5. The delivery system as claimed in claim 4 wherein a distal end of the sleeve extends to a distal end of the balloon and the sleeve has a slit or a region of weakness which splits or ruptures on inflation of the balloon.

6. The delivery system as claimed in claim 3 wherein the sleeve is configured to split or rupture when pulled proximally away from the catheter distal tip.

7. The delivery system as claimed in claim 6 wherein a distal end of the sleeve extends to a distal end of the balloon and the sleeve has a slit or a region of weakness which splits or ruptures when the sleeve is pulled away from the catheter distal tip.

8. The delivery system as claimed in claim 1 wherein the protective sleeve has a tapered distal end section.

9. The delivery system as claimed in claim 1 wherein the spacer comprises at least one ridge or rib extending along the interior surface of the protective sleeve.

10. The delivery system as claimed in claim 9 wherein there are at least two ridges or ribs which are spaced equidistantly from one another.

11. The delivery system as claimed in claim 1 wherein the inner surface of the protective sleeve comprises a lubricious coating.

12. The delivery system as claimed in claim 1 wherein the sleeve is retractable prior to, during, or after expansion of the balloon.

13. The delivery system as claimed in claim 12 wherein the protective sleeve and the catheter are coupled for delivery and de-coupled for deployment of the balloon.

14. A method of performing a balloon dilation procedure within a vascular system comprising:

provided a drug coated balloon mounted on a catheter with a protective sleeve surrounding the drug coating on the balloon, the balloon having a wrapped or folded delivery configuration and an expanded deployed configuration, wherein the protective sleeve further comprises a spacer configured to at least partially space-apart the protective sleeve from the drug coating on the balloon when the balloon is in the wrapped or folded configuration, and wherein the spacer extends longitudinally along an interior surface of the protective sleeve;

advancing the catheter to a treatment location with the balloon in the delivery configuration;

removing the sleeve from the balloon to expose the drug coated surface of the balloon; and carrying out a treatment using the drug coated balloon.

15. The method as claimed in claim 14 comprising the step of applying a force to the sleeve to remove the sleeve from the balloon.

16. The method as claimed in claim 15 comprising at least partially inflating the balloon to remove the sleeve from the balloon.

17. The method as claimed in claim 15 comprising pulling the sleeve proximally to remove the sleeve from the balloon.

18. The method as claimed in claim 17 wherein the sleeve is removed prior to inflation of the balloon.

* * * * *